(12) United States Patent
Liu et al.

(10) Patent No.: US 8,030,271 B2
(45) Date of Patent: Oct. 4, 2011

(54) COMPOSITIONS AND METHODS FOR BUCCAL DELIVERY OF HUMAN GROWTH HORMONE

(75) Inventors: Puchun Liu, Chappaqua, NY (US); Steven Dinh, Briarcliff Manor, NY (US); Jongbin Lee, New City, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 113 days.

(21) Appl. No.: 11/993,941

(22) PCT Filed: Jul. 5, 2006

(86) PCT No.: PCT/US2006/026262
§ 371 (c)(1),
(2), (4) Date: Dec. 26, 2007

(87) PCT Pub. No.: WO2007/005995
PCT Pub. Date: Jan. 11, 2007

(65) Prior Publication Data
US 2008/0207513 A1      Aug. 28, 2008

Related U.S. Application Data

(60) Provisional application No. 60/697,018, filed on Jul. 5, 2005.

(51) Int. Cl.
*A61K 38/27* (2006.01)
*A61P 3/04* (2006.01)

(52) U.S. Cl. .................................................. 514/5.1

(58) Field of Classification Search .................. None
See application file for complete search history.

(56) References Cited

U.S. PATENT DOCUMENTS

| | | | |
|---|---|---|---|
| 4,658,021 A | 4/1987 | Goeddel et al. | |
| 4,670,393 A | 6/1987 | Seeburg | |
| 4,764,378 A * | 8/1988 | Keith et al. | 424/435 |
| 4,963,367 A | 10/1990 | Ecanow | |
| 5,284,657 A | 2/1994 | Lu et al. | |
| 5,424,199 A | 6/1995 | Goeddel et al. | |
| 5,629,020 A | 5/1997 | Leone-Bay et al. | |
| 5,633,352 A | 5/1997 | Dalb.o slashed.ge et al. | |
| 5,795,745 A | 8/1998 | Goeddel et al. | |
| 6,161,731 A * | 12/2000 | Sigg | 222/158 |
| 6,566,328 B1 | 5/2003 | Rosen et al. | |
| 6,780,613 B1 | 8/2004 | Wells et al. | |
| 7,049,283 B2 * | 5/2006 | Ault et al. | 514/2 |
| 7,659,311 B2 * | 2/2010 | Bay et al. | 514/563 |
| 2003/0059376 A1 * | 3/2003 | Libbey et al. | 424/46 |
| 2003/0134861 A1 | 7/2003 | Doherty et al. | |

FOREIGN PATENT DOCUMENTS

| | | |
|---|---|---|
| WO | WO-03/057650 A1 | 7/2003 |
| WO | WO-2005/107462 | 11/2005 |
| WO | WO-2005112633 | 12/2005 |
| WO | WO-2005117854 | 12/2005 |
| WO | WO 2008/027854 | 3/2008 |
| WO | WO 2008/112836 | 9/2008 |

OTHER PUBLICATIONS

U.S. Appl. No. 60/569,476, filed May 6, 2004.
U.S. Appl. No. 60/619,418, filed Oct. 15, 2004.
Heffernan, M.A., et al., "Effects of Oral Administration of a Synthetic Fragment of Human Growth Hormone on Lipid Metabolism," The American Journal of Physiology—Endocronology & Metabolism, vol. 279, No. 3, Sep. 2000, p. E501-E507.

* cited by examiner

*Primary Examiner* — Robert Landsman
(74) *Attorney, Agent, or Firm* — Blank Rome LLP

(57) ABSTRACT

The present invention provides pharmaceutical compositions for buccal delivery of human growth hormone (hGH) comprising a delivery agent and hGH. The compositions of the present invention provide improved delivery of hGH compared to comparable oral compositions, resulting in increased serum concentrations of hGH. The present invention further provides for methods of stimulating tissue growth in an animal by buccally co-administering hGH and a delivery agent.

12 Claims, 4 Drawing Sheets

COMPOSITIONS AND METHODS FOR BUCCAL DELIVERY OF HUMAN GROWTH HORMONE

CROSS-REFERENCE TO RELATED APPLICATIONS

This application is a 371 national phase of International Application No. PCT/US2006/026262, filed Jul. 5, 2006, which claims the benefit of U.S. Provisional Application No. 60/697,018, filed Jul. 5, 2005. International Application No. PCT/US2006/026262 published in English on Jan. 11, 2007 under Publication No. WO 2007/005995. These applications are hereby incorporated by reference in their entirety.

FIELD OF THE INVENTION

The present invention relates to buccal delivery of a human growth hormone (hGH) component with a delivery agent, pharmaceutical compositions for buccal administration comprising a hGH component and a delivery agent, and methods of treating growth hormone deficiency in an animal by buccally co-administering a hGH component and a delivery agent.

BACKGROUND OF THE INVENTION

Pituitary disorders such as growth hormone deficiency (GHD), also referred to as Somatotropin Deficiency Syndrome, effect the production and secretion of growth hormone often resulting in short stature and other physical ailments. GHD results in lower levels of endogenous growth hormone, which causes numerous adverse affects on body processes. Growth hormone is critical to tissue growth, and is known to stimulate the growth of such tissue as skeletal, skeletal muscle and organ. Human growth hormone has also been implicated in the metabolism of fat, carbohydrates, proteins and minerals such as potassium and phosphorus.

Human growth hormone (hGH) is a naturally occurring human protein secreted by the pituitary gland which consists of 191 amino acids and has a molecular weight of about 22,000 daltons. hGH may isolated from in its natural form from the pituitary gland of human cadavers, or may be produced recombinantly known genetic engineering techniques. Recombinant production of hGH can yield a variety of hGH species, including a 191 amino acid native species (commonly known as Somatropin), as described for example in U.S. Pat. Nos. 4,670,393, 5,424,199, 5,633,352 and 5,795,745 (the disclosures of which are hereby incorporated by reference) or a 192 amino acid species, met-hGH, having N-terminal methionine (met) (commonly known as Somatrem), such as that described in U.S. Pat. No. 4,658,021, which is hereby incorporated by reference.

Recombinant hGH (both the 191 and 192 amino acid species) has been approved by the FDA for a number of treatments, including the treatment of children and adults suffering from GHD, and the treatment of wasting in individuals suffering from AIDS. One example of approved hGH is Nutropin®, commercially available from Genentech (South San Francisco, Calif.) which consists of 191 amino acids and has been approved for the treatment of GHD, Turner Syndrome and chronic renal failure in children and for the treatment of adults suffering from GHD. Currently, all FDA approved hGH compositions are administered subcutaneously by injection, three times a week or once daily in order to maintain suitable serum levels of hGH.

Buccal delivery is a more preferable method of administering drugs and offers several advantages over subcutaneous injection. Typically, a buccal dosage form is placed in the buccal cavity between the gum and the cheek, where it dissolves in the patient's saliva, releasing the drug into the buccal cavity in close proximity to the capillary bed of the oral mucosa. The drug then enters the blood in the capillary bed by diffusion through the mucosal tissue and is distributed in the bloodstream to the rest of the body.

Buccal administration is less invasive and results in greater patient compliance compared to subcutaneous injection. Furthermore, unlike oral administration, buccal administration avoids the possibility that the drug will be destroyed in the gastrointestinal tract before it can be absorbed, and eliminates first-pass inactivation in the liver after absorption.

Therefore, there is a need for a human growth hormone formulation which can be buccally administered.

SUMMARY OF THE INVENTION

The present invention relates to a pharmaceutical composition for buccal administration comprising (a) a delivery agent and (b) a human growth hormone (hGH) component. The pharmaceutical composition of the present invention may be formulated into a dosage unit form, such as a buccal dosage unit form. Surprisingly, it has been found that the buccal compositions of the present invention provide improved delivery of hGH as compared to comparable orally administered compositions, i.e. compositions that are swallowed.

Another embodiment is a method for administering a hGH component to a subject in need thereof by buccally co-administering a delivery agent and the hGH component. Preferably, a pharmaceutical composition or unitary dosage form containing both components is administered. A therapeutically effective amount of the components is preferably administered.

Yet another embodiment is a method of stimulating new tissue growth in a subject in need thereof by buccally co-administering an effective amount of a delivery agent and a hGH component. Preferably, a pharmaceutical composition or unitary dosage form containing both components is administered. A therapeutically effective amount of the components is preferably administered.

Yet another embodiment is a method of treating growth hormone deficiency (GDH) in a subject in need thereof by buccally co-administering an effective amount of a delivery agent, and a hGH component. Preferably, a pharmaceutical composition or unitary dosage form containing both components is administered.

Yet another embodiment is a method for treating Turner syndrome, idiopathic short stature, renal failure, AIDS-related wasting and lipodystrophy, decreased thymic function (including decreased thymic function associated with subjects receiving antiretroviral therapy), age-related decreases in muscle mass and strength, decreased lipolysis, Crohn's disease, idiopathic related cardiomyopathy, dilated cardiomyopathy, ischemic heart disease, hypopituitarism, decreased cardiac function, fluids imbalance, osteoporosis, decreased lung function, decreased immunity, lack of REM sleep, decreased sense of well being, Prader-Willi syndrome, catabolic problems associated with subjects in intensive care environments and subjects who have burns, cystic fibrosis, inflammatory bowel disease, fertility problems, and Downs syndrome and achondroplasia. The method includes bucally co-administering to a subject an effective amount of a delivery agent, and a hGH component. Preferably, a pharmaceutical composition or unitary dosage form containing both components is administered.

Yet another embodiment is a method for treating fibromialgia, chronic fatigue, lupus and other connective tissue disorders comprising administering compositions of the present invention. In one embodiment, provided is a method of treating somatotropin (growth hormone) deficiency syndrome (SDS) as a result of pituitary disease, hypothalamic disease, surgery, radiation therapy, or injury comprising administering compositions of the present invention.

In an alternative embodiment, provided is a method of treating aging effects, including effects resulting from a failure of the pituitary to release vital amounts of HGH. In an alternative embodiment is a method of treating decreased physical mobility, lower energy and increased risk of cardiovascular disease comprising administering compositions of the present invention.

DETAILED DESCRIPTION OF THE INVENTION

Figure 1:
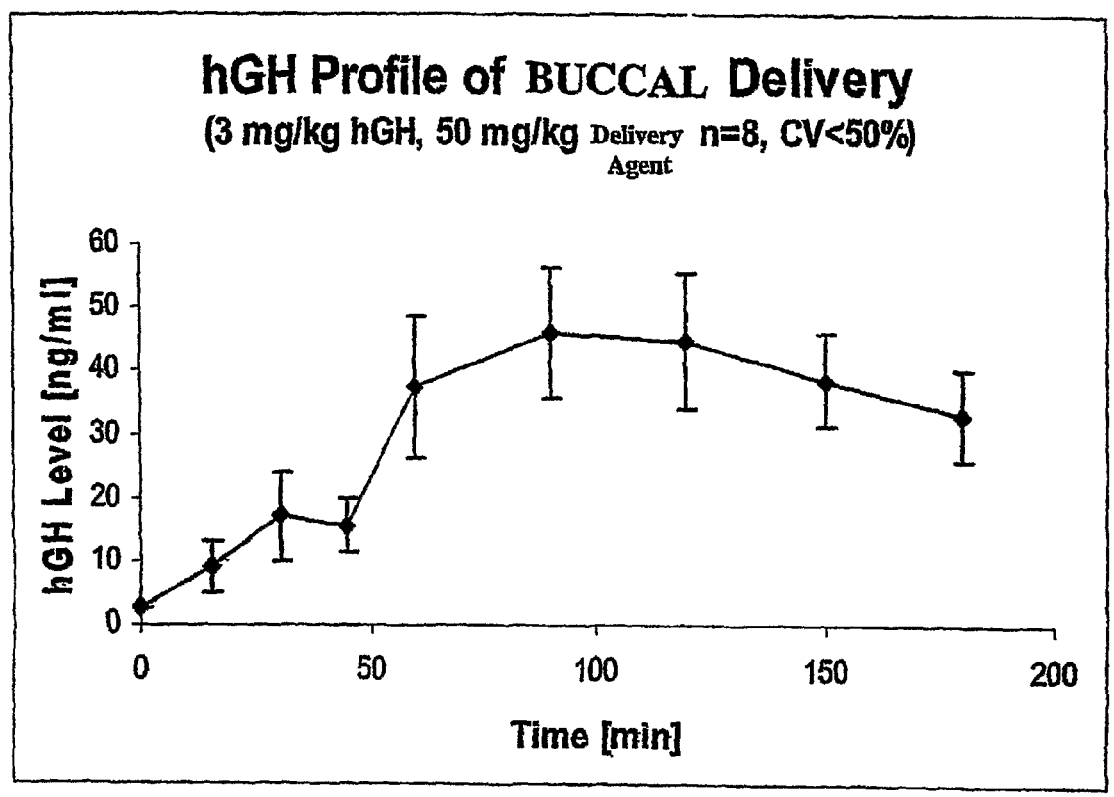
FIG. 1 is a graph of mean human growth hormone (hGH) concentrations over time after buccal administration of a solid dosage form containing 3 mg/kg hGH with 50 mg/kg monosodium 8-(4-Hydroxyphenoxy)octanoic acid in beagles.

Unless otherwise specified, the term "substituted" as used herein includes, but is not limited to, substitution with any one or any combination of the following substituents: halogens, hydroxide, $C_1$-$C_4$ alkyl, and $C_1$-$C_4$ alkoxy.

The terms "alkyl", "alkoxy", "alkylene", "alkenylene", "alkyl(arylene)", and "aryl(alkylene)" include, but are not limited to, linear and branched alkyl, alkoxy, alkylene, alkenylene, alkyl(arylene), and aryl(alkylene) groups, respectively.

The term "delivery agent" includes, but is not limited to, any of the delivery agent compounds disclosed herein.

The term "4-MOAC" refers to 8-(N-2-hydroxy-4-methoxybenzoyl)-aminocaprylic acid and pharmaceutically acceptable salts thereof. Unless otherwise noted, the term "4-MOAC" refers to all forms of 4-MOAC, including all amorphous and polymorphic forms of 4-MOAC.

The term "NAC" as used herein refers to N-(8-[2-hydroxybenzoyl]-amino) caprylic acid and pharmaceutically acceptable salts thereof, including its monosodium salt. Unless otherwise noted, the term "NAC" refers to all forms of NAC, including all amorphous and polymorphic forms of NAC. The term "SNAC" as used herein refers to the monosodium salt of NAC, including all amorphous and polymorphic forms of it (such as those described in U.S. Provisional Application Nos. 60/569,476, filed May 6, 2004, and 60/619,418, filed Oct. 15, 2004, and International Application No. PCT/US05/16126, filed May 6, 2005, each of which are hereby incorporated by reference), unless otherwise indicated.

The term "NAD" as used herein refers to N-(8-[2-hydroxybenzoyl]-amino) decanoic acid and pharmaceutically acceptable salts thereof, including its monosodium salt. Unless otherwise noted, the term "NAD" refers to all forms of NAD, including all amorphous and polymorphic forms of NAD. The term "SNAD" as used herein refers to the monosodium salt of NAD, including all amorphous and polymorphic forms of it.

The term "5-CNAC" refers to N-(8-[2-hydroxy-5-chlorobenzoyl]-amino)octanoic acid (also known as 8-(N-2-hydroxy-5-chlorobenzoyl)aminocaprylic acid)) and pharmaceutically acceptable salts thereof, including its monosodium salt. Unless otherwise noted, the term "5-CNAC" refers to all forms of 5-CNAC, including all amorphous and polymorphic forms of it.

The term "4-CNAB" refers to 4-[(2-hydroxy-4-chlorobenzoyl)amino]butanoate (also known as 4-[(4-chloro-2-hydroxybenzoyl)amino]butanoic acid) and pharmaceutically acceptable salts thereof, including its monosodium salt. Unless otherwise noted, the term "4-CNAB" refers to all forms of 4-CNAB, including all amorphous and polymorphic forms of 4-CNAB. The term "mono-sodium 4-CNAB" refers to monosodium 4-[(2-hydroxy-4-chlorobenzoyl)amino]butanoate, including anhydrous, monohydrate, and isopropanol solvates thereof and amorphous and polymorphic forms thereof (including those described in International Publication No. WO 03/057650 which is hereby incorporated by reference), unless otherwise indicated.

An "effective amount of human growth hormone" or an "effective amount of a hGH component" is an amount effective to treat or prevent a condition or to stimulate tissue growth in a living organism to whom it is administered over some period of time, e.g., provides a therapeutic effect during a desired dosing interval. An "effective amount of a delivery agent" is an amount of the delivery agent which enables and/or facilitates the absorption of human growth hormone.

As used herein and in the appended claims, the singular forms "a," "an," "and," and "the," include plural referents unless the context clearly indicates otherwise. Thus, for example, reference to "a molecule: includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

The term "subject" as used herein refers to a mammal and preferably a human.

The phrase "pharmaceutically acceptable" refers to components or compositions that are physiologically tolerable when administered to a mammal, such as a human.

The terms "buccal administration" and "buccally administering" include administration by adsorption through any surface inside the mouth or upper throat (such as the cheek (e.g., the inner cheek lining), gums, palate, tongue, tonsils, periodontal tissue, lips, and/or the mucosa of the mouth and pharynx). These terms, for example, include sublingual and intraoral administration, and administration in the buccal cavity between the gum and the cheek.

The term "Growth Hormone" (GH) and human growth hormone component includes any form of, for example, human GH, Recombinant GH, bovine GH, porcine GH, primate GH, and GH derivatives, mimetics, and analogs thereof which have a similar effect as GH.

The term pharmaceutically acceptable salts include salts that are tolerable when administered to a subject, such as a human.

Delivery Agent Compounds

Suitable delivery agents include those having the following structure and pharmaceutically acceptable salts thereof:

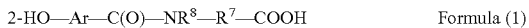

$$2\text{-HO}—Ar—C(O)—NR^8—R^7—COOH \quad \text{Formula (1)}$$

wherein:

Ar is phenyl or naphthyl, optionally substituted with OH, halogen, $C_1$-$C_4$ alkyl, $C_1$-$C_4$ alkenyl, $C_1$-$C_4$ alkoxy or $C_1$-$C_4$ haloalkoxy;

$R^7$ is $C_4$-$C_{20}$ alkyl, $C_4$-$C_{20}$ alkenyl, phenyl, naphthyl, ($C_1$-$C_{10}$ alkyl) phenyl, ($C_1$-$C_{10}$ alkenyl)phenyl, ($C_1$-$C_{10}$ alkyl) naphthyl, ($C_1$-$C_{10}$ alkenyl) naphthyl, phenyl($C_1$-$C_{10}$ alkyl), phenyl($C_1$-$C_{10}$ alkenyl), naphthyl($C_1$-$C_{10}$ alkyl), or naphthyl ($C_1$-$C_{10}$ alkenyl);

$R^8$ is hydrogen, $C_1$ to $C_4$ alkyl, $C_2$ to $C_4$ alkenyl, $C_1$ to $C_4$ alkoxy, $C_1$-$C_4$ or haloalkoxy;

$R^7$ is optionally substituted with $C_1$ to $C_4$ alkyl, $C_2$ to $C_4$ alkenyl, $C_1$ to $C_4$ alkoxy, $C_1$-$C_4$ haloalkoxy, —OH, —SH, and —$CO_2R^9$ or any combination thereof;

$R^9$ is hydrogen, $C_1$ to $C_4$ alkyl or $C_2$ to $C_4$ alkenyl; and $R^7$ is optionally interrupted by oxygen, nitrogen, sulfur or any combination thereof;

with the proviso that the compounds are not substituted with an amino group in the position alpha to the acid group or salts thereof.

According to one embodiment, Ar is substituted with a halogen. Preferably, $R^7$ is $C_4$-$C_{20}$ alkyl or phenyl($C_1$-$C_{10}$ alkyl). More preferably $R^7$ is $C_5$-$C_{10}$ alkyl or phenyl($C_2$ alkyl). Most preferably, $R^7$ is $C_7$-$C_9$ alkyl or phenyl($C_2$ alkyl).

Other suitable delivery agents include those having the following structure and pharmaceutically acceptable salts thereof:

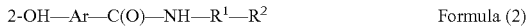

$$2\text{-OH}—Ar—C(O)—NH—R^1—R^2 \quad \text{Formula (2)}$$

wherein

Ar is phenyl or naphthyl;

Ar is optionally substituted with $C_1$-$C_4$ alkyl, $C_1$-$C_4$ alkoxy, $C_2$-$C_4$ alkenyl, $C_2$-$C_4$ alkynyl, aryl, aryloxy, a heterocyclic ring, $C_5$-$C_7$ carbocyclic ring, halogen, —OH, —SH, $CO_2R^6$, —$NR^7R^8$, or —$N^+R^7R^8R^9Y^-$;

(a) $R^1$ is $C_1$-$C_{16}$ alkylene, $C_2$-$C_{16}$ alkenylene, $C_2$-$C_{16}$ alkynylene, $C_6$-$C_{16}$ arylene, ($C_1$-$C_{16}$ alkyl)arylene, or aryl ($C_1$-$C_{16}$ alkylene);

$R^2$ is —$NR^3R^4$ or —$N^+R^3R^4R^5Y^-$;

$R^3$ and $R^4$ are independently hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^5$ is independently hydrogen; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

(b) $R^1$, $R^2$, and $R^5$ are as defined above; and $R^3$ and $R^4$ are combined to form a 5, 6 or 7-membered heterocyclic ring; or 5, 6 or 7-membered heterocyclic ring substituted with a $C_1$-$C_6$ alkyl, $C_1$-$C_6$ alkoxy, aryl, aryloxy, oxo group or carbocyclic ring; or (c) $R^2$ and $R^5$ are as defined above; and $R^1$ and $R^3$ are combined to form a 5, 6 or 7-membered heterocyclic ring; or 5, 6 or 7-membered heterocyclic ring substituted with a $C_1$-$C_6$ alkyl, alkoxy, aryl, aryloxy, or oxo group or carbocyclic ring;

$R^4$ is hydrogen; oxygen; hydroxy; substituted or unsubstituted $C_1$-$C_{16}$ alkyl; substituted or unsubstituted $C_2$-$C_{16}$ alkenyl; substituted or unsubstituted $C_2$-$C_{16}$ alkynyl; substituted or unsubstituted aryl; substituted or unsubstituted alkylcarbonyl; substituted or unsubstituted arylcarbonyl; substituted or unsubstituted alkanesulfinyl; substituted or unsubstituted arylsulfinyl; substituted or unsubstituted alkanesulfonyl; substituted or unsubstituted arylsulfonyl; substituted or unsubstituted alkoxycarbonyl; substituted or unsubstituted aryloxycarbonyl;

$R^6$ is hydrogen; $C_1$-$C_4$ alkyl; $C_1$-$C_4$ alkyl substituted halogen or —OH; $C_2$-$C_4$ alkenyl; or $C_2$-$C_4$ alkenyl substituted halogen or —OH;

$R^7$, $R^8$, and $R^9$ are independently hydrogen; oxygen; $C_1$-$C_4$ alkyl; $C_1$-$C_4$ alkyl substituted with halogen or —OH; $C_2$-$C_4$ alkenyl; or $C_2$-$C_4$ alkenyl substituted with halogen or —OH; and Y is halogen, hydroxide, sulfate, nitrate, phosphate, alkoxy, perchlorate, tetrafluoroborate, or carboxylate. A non-limiting example of a suitable carboxylate is acetate.

The term "substituted" as used herein with respect to the compounds of formula (2) includes, but is not limited to, hydroxyl and halogen.

In one embodiment, Ar is unsubstituted phenyl or phenyl substituted with one or more of $C_1$-$C_4$ alkyl, $C_1$-$C_4$ alkoxy, or halogen. More preferably, Ar is a phenyl substituted with methoxy, Cl, F or Br, and even more preferably, Ar is a phenyl substituted with Cl.

In another embodiment, $R^1$ is $C_1$-$C_{12}$ alkyl, $C_2$-$C_8$ alkyl, $C_2$-$C_6$ alkyl, or $C_6$ alkyl.

In another embodiment, $R^3$ and $R^4$ are independently H or $C_1$-$C_2$ alkyl; or further $R^3$ and $R^4$ are not both H; or further $R^3$ and $R^4$ are independently methyl or ethyl; and more preferably $R^3$ and $R^4$ are both methyl.

Other suitable delivery agents include those having the following structure and pharmaceutically acceptable salts thereof:

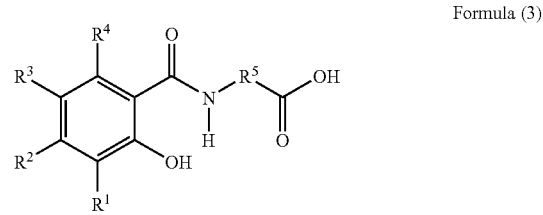

Formula (3)

wherein:

$R^1$, $R^2$, $R^3$, and $R^4$ are independently hydrogen, —OH, —$NR^6R^7$, halogen, $C_1$-$C_4$ alkyl, or $C_1$-$C_4$ alkoxy;

$R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and $R^6$ and $R^7$ are independently hydrogen, oxygen, or $C_1$-$C_4$ alkyl.

According to one embodiment, $R^1$, $R^2$, $R^3$, and $R^4$ are H, and $R^5$ is unsubstituted $C_2$-$C_{16}$ alkylene. In one embodiment, $R^1$, $R^2$, $R^3$, and $R^4$ are H, and $R^5$ is unsubstituted $C_4$-$C_{14}$ alkylene. $R^1$, $R^2$, $R^3$, and $R^4$ are H, and $R^5$ is unsubstituted $C_6$-$C_{12}$ alkylene. In one embodiment, $R^1$, $R^2$, $R^3$, and $R^4$ are H, and $R^5$ is unsubstituted $C_6$-$C_{10}$ alkylene.

The term "substituted" as used with respect to formula (3) includes, but is not limited to, substitution with any one or any combination of the following substituents: halogens, hydroxide, $C_1$-$C_4$ alkyl, and $C_1$-$C_4$ alkoxy.

Other suitable delivery agents include those having the following structure and pharmaceutically acceptable salts thereof:

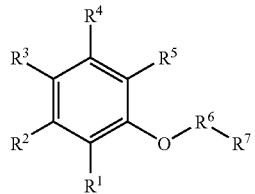

Formula (4)

wherein:
(a) $R^1$, $R^2$, $R^3$, and $R^4$ are independently H, —OH, halogen, $C_1$-$C_4$ alkyl, $C_1$-$C_4$ alkenyl, $C_1$-$C_4$ alkoxy, —C(O)$R^8$, —NO$_2$, —NR$^9$R$^{10}$, or —N$^+$R$^9$R$^{10}$R$^{11}$(Y$^-$);

$R^8$ is hydrogen, —OH, $C_1$-$C_6$ alkyl, $C_1$-$C_4$ alkyl substituted with halogen or —OH, $C_2$-$C_4$ alkenyl unsubstituted or substituted with halogen or —OH, or —NR$^{14}$R$^{15}$;

$R^9$, $R^{10}$, and $R^{11}$ are independently hydrogen, oxygen, $C_1$-$C_4$ alkyl unsubstituted or substituted with halogen or —OH, $C_2$-$C_4$ alkenyl unsubstituted or substituted with halogen or —OH;

Y is halide, hydroxide, sulfate, nitrate, phosphate, alkoxy, perchlorate, tetrafluoroborate, carboxylate, mesylate, fumerate, malonate, succinate, tartrate, acetate, gluconate, maleate;

$R^5$ is H, —OH, —NO$_2$, halogen, CF$_3$, —NR$^{14}$R$^{15}$, —N$^+$R$^{14}$R$^{15}$R$^{16}$(Y$^-$), amide, $C_1$-$C_{12}$ alkoxy, $C_1$-$C_{12}$ alkyl, $C_2$-$C_{12}$ alkenyl, carbamate, carbonate, urea, or —C(O)$R^{22}$; $R^5$ is optionally substituted with halogen, —OH, —SH, or —COOH; $R^5$ is optionally interrupted by O, N, S, or —C(O)—;

$R^{14}$, $R^{15}$, and $R^{16}$ are independently H or $C_1$-$C_{10}$ alkyl;

$R^{22}$ is H, $C_1$-$C_6$ alkyl, —OH, —NR$^{14}$R$^{15}$;

$R^6$ is substituted or unsubstituted $C_1$-$C_{16}$ alkylene, $C_2$-$C_{16}$ alkenylene, $C_2$-$C_{16}$ alkynylene, $C_5$-$C_{16}$ arylene, ($C_1$-$C_{16}$ alkyl) arylene or aryl($C_1$-$C_{16}$ alkylene); $R^6$ is optionally substituted with $C_1$-$C_7$ alkyl or $C_1$-$C_7$ cycloalkyl;

$R^7$ is —NR$^{18}$R$^{19}$ or —N$^+$R$^{18}$R$^{19}$R$^{20}$Y$^-$;

$R^{18}$ and $R^{19}$ are independently hydrogen, oxygen, hydroxy, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy)carbonyl), or substituted or unsubstituted aryloxycarbonyl, or substituted or unsubstituted $C_5$-$C_7$ heterocyclic ring (i.e., 5, 6, or 7-membered heterocyclic ring), wherein the substitutions may be halogen or —OH; and $R^{20}$ is independently hydrogen, substituted or unsubstituted $C_1$-$C_{16}$ alkyl, substituted or unsubstituted $C_2$-$C_{16}$ alkenyl, substituted or unsubstituted $C_2$-$C_{16}$ alkynyl, substituted or unsubstituted aryl, substituted or unsubstituted alkylcarbonyl (e.g. substituted or unsubstituted ($C_{1-6}$ alkyl)carbonyl), substituted or unsubstituted arylcarbonyl, substituted or unsubstituted alkanesulfinyl (e.g. substituted or unsubstituted ($C_{1-6}$ alkane)sulfinyl), substituted or unsubstituted arylsulfinyl, substituted or unsubstituted alkanesulfonyl (e.g. substituted or unsubstituted ($C_{1-6}$ alkane)sulfonyl), substituted or unsubstituted arylsulfonyl, substituted or unsubstituted alkoxycarbonyl (e.g. substituted or unsubstituted ($C_{1-6}$ alkoxy) carbonyl), or substituted or unsubstituted aryloxycarbonyl; or (b) $R^1$-$R^{16}$ and $R^{20}$ are as defined above; and $R^{18}$ and $R^{19}$ combine to form a 5, 6, or 7-membered heterocyclic ring optionally interrupted with an oxo group and unsubstituted or substituted with $C_1$-$C_6$ alkyl, $C_1$-$C_6$ alkoxy, aryl, aryloxy, or carbocyclic ring.

According to one embodiment, $R^7$ is morpholino, morpholinium salt, or diethanolamino.

According to another embodiment, $R^6$ is a $C_1$-$C_{16}$ alkylene and $R^7$ is morpholino or a morpholinium salt. Preferably, $R^6$ is $C_4$-$C_{12}$ alkylene, such as an unsubstituted $C_4$-$C_{12}$ alkylene. More preferably, $R^6$ is $C_4$-$C_{10}$, $C_4$-$C_8$, or $C_6$-$C_8$ alkylene, such as an unsubstituted $C_4$-$C_{10}$, $C_4$-$C_8$, or $C_6$-$C_8$ alkylene. According to one embodiment, one of $R^1$-$R^5$ is hydroxy, for example, $R^1$ can be hydroxy.

According to yet another embodiment, when $R^6$ is a $C_1$-$C_{10}$ alkylene, at most one of $R^2$ and $R^4$ is halogen. According to another embodiment, $R^6$ is a $C_8$-$C_{16}$, $C_9$-$C_{16}$, $C_{10}$-$C_{16}$, or $C_{11}$-$C_{16}$ alkylene. For instance, $R^6$ may be a $C_8$, $C_9$, $C_{10}$, $C_{11}$, or $C_{12}$ alkylene (e.g., a normal $C_8$-$C_{12}$ alkylene). According to yet another embodiment, at most one of $R^1$ and $R^5$ is alkyl.

According to yet another embodiment, $R^1$ is hydroxy and $R^2$, $R^3$, $R^4$, and $R^5$ are independently hydrogen or halogen.

According to yet another embodiment, $R^2$ is hydroxy and $R^1$, $R^3$, $R^4$, and $R^5$ are independently hydrogen or halogen.

According to yet another embodiment, $R^3$ is hydroxy and $R^1$, $R^2$, $R^4$, and $R^5$ are independently hydrogen or halogen.

In a preferred embodiment, halogen is F, Cl or Br, more preferably F or Cl, and even more preferably Cl.

According to yet another embodiment, $R^6$ is $C_1$-$C_{16}$ alkylene, ($C_1$-$C_{16}$ alkyl) arylene or aryl($C_1$-$C_{16}$ alkylene). More preferably $R^6$ is $C_1$-$C_{12}$ alkylene, more preferably $C_3$-$C_{10}$ alkylene, more preferably $C_4$-$C_{10}$ or $C_4$-$C_8$ alkylene, and more preferably $C_6$-$C_8$ alkylene. More preferably, $R^6$ is unsubstituted.

According to yet another embodiment, $R^7$ is —NR$^{18}$R$^{19}$ and $R^{18}$ and $R^{19}$ are independently $C_1$-$C_4$ alkyl (e.g., methyl, ethyl, propyl, or butyl) substituted with —OH. In another embodiment, $R^7$ is —NR$^{18}$R$^{19}$ and $R^{18}$ and $R^{19}$ combine to form a six membered heterocyclic ring substituted with an oxo group.

According to one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene, and $R^7$ is $NR^{18}R^{19}$ wherein $R^{18}$ and $R^{19}$ combine to form a 5, 6, or 7 membered heterocyclic ring.

According to another preferred embodiment, one of $R^3$, $R^4$, and $R^5$ is hydroxy and the others are independently halogen or hydrogen; $R^1$ and $R^2$ are independently halogen or hydrogen; $R^6$ is $C_1$-$C_{16}$ alkylene; and $R^7$ is $NR^{18}R^{19}$ wherein $R^{18}$ and $R^{19}$ combine to form a 5, 6, or 7 membered heterocyclic ring. $R^6$ is preferably $C_6$-$C_{16}$, $C_6$-$C_{10}$, $C_8$-$C_{16}$, $C_{10}$-$C_{16}$, or $C_4$-$C_8$ alkylene, such as unsubstituted $C_6$-$C_{16}$, $C_6$-$C_{10}$, $C_8$-$C_{16}$, $C_{10}$-$C_{16}$, or $C_4$-$C_8$ alkylene. Preferably, $R^{18}$ and $R^{19}$ form a morpholino or imidazole.

In another preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, $R^1$, $R^2$, $R^4$, $R^5$ are independently halogen or hydrogen; $R^3$ is —OH, or —OCH$_3$; and $R^7$ is $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

According to one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_6$ alkylene or aryl substituted $C_1$-$C_{12}$ alkyl; and $R^7$ is —NR$^{18}$R$^{19}$ wherein $R^{18}$ and $R^{19}$ combine to form a 5, 6, or 7 membered heterocyclic ring or $N^+R^{18}R^{19}R^{20}$ ($Y^-$) wherein $R^{18}$ and $R^{19}$ are hydroxy substituted $C_1$-$C_{16}$ alkyl and $R^{20}$ is hydrogen.

In another preferred embodiment, the citrate salt of the delivery agent is used.

Other suitable delivery agents include those having the following structure and pharmaceutically acceptable salts thereof:

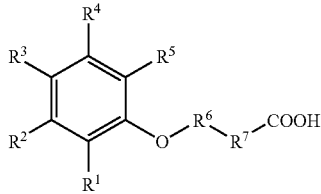

Formula (5)

wherein:

$R^1$, $R^2$, $R^3$, and $R^4$ are independently H, —OH, halogen, $C_1$-$C_4$ alkyl, $C_2$-$C_4$ alkenyl, $C_1$-$C_4$ alkoxy, —C(O)R$^8$, —NO$_2$, —NR$^9$R$^{10}$, or —N$^+$R$^9$R$^{10}$R$^{11}$ (R$^{12}$)$^-$;

$R^5$ is H, —OH, —NO$_2$, halogen, —CF$_3$, —NR$^{14}$R$^{15}$, —N$^+$R$^{14}$R$^{15}$R$^{16}$ (R$^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)R$^{18}$;

$R^5$ is optionally substituted with halogen, —OH, —SH, or —COOH;

$R^5$ is optionally interrupted by O, N, S, or —C(O)—;

$R^6$ is a $C_1$-$C_{12}$ alkylene, $C_2$-$C_{12}$ alkenylene, or arylene;

$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^8$;

$R^6$ is optionally interrupted by O or N;

$R^7$ is a bond or arylene;

$R^7$ is optionally substituted with —OH, halogen, —C(O)CH$_3$, —NR$^{10}$R$^{11}$, or —N$^+$R$^{10}$R$^{11}$R$^{12}$ (R$^{13}$)$^-$;

$R^8$ is H, $C_1$-$C_4$ alkyl, $C_2$-$C_4$ alkenyl, or —NH$_2$;

$R^9$, $R^{10}$, $R^{11}$, and $R^{12}$ independently H or $C_1$-$C_{10}$ alkyl;

$R^{13}$ is a halide, hydroxide, sulfate, tetrafluoroborate, or phosphate; and $R^{14}$, $R^{15}$ and $R^{16}$ are independently H, $C_1$-$C_{10}$ alkyl, $C_1$-$C_{10}$ alkyl substituted with —COOH, $C_2$-$C_{12}$ alkenyl, $C_2$-$C_{12}$ alkenyl substituted with —COOH, —C(O)R$^{17}$;

$R^{17}$ is —OH, $C_1$-$C_{10}$ alkyl, or $C_2$-$C_{12}$ alkenyl; and $R^{18}$ is H, $C_1$-$C_6$ alkyl, —OH, —NR$^{14}$R$^{15}$, or N$^+$R$^{14}$R$^{15}$R$^{16}$ (R$^{13}$).

According one embodiment, (1) when $R^1$, $R^2$, $R^3$, $R^4$, and $R^5$ are H, and $R^7$ is a bond then $R^6$ is not a $C_1$-$C_6$, $C_9$ or $C_{10}$ alkyl;

(2) when $R^1$, $R^2$, $R^3$, and $R^4$ are H, $R^5$ is —OH, $R^7$ is a bond then $R^6$ is not a $C_1$-$C_3$ alkyl;

(3) when at least one of $R^1$, $R^2$, $R^3$, and $R^4$ is not H, $R^5$ is —OH, $R^7$ is a bond, then $R^6$ is not a $C_1$-$C_4$ alkyl;

(4) when $R^1$, $R^2$, and $R^3$ are H, $R^4$ is —OCH$_3$, $R^5$ is —C(O)CH$_3$, and $R^6$ is a bond then $R^7$ is not a $C_3$ alkyl; and (5) when $R^1$, $R^2$, $R^4$, and $R^5$ are H, $R^3$ is —OH, and $R^7$ is a bond then $R^6$ is not a methyl.

According one preferred embodiment, $R^1$ is hydrogen; $R^2$, $R^3$, and $R^4$ are independently hydrogen, halogen, —OH, or —OCH$_3$; $R^5$ is hydrogen, —OH, or —C(O)CH$_3$; $R^6$ is $C_1$-$C_{12}$ alkylene, and $R^7$ is a bond or para-phenylene. $R^7$ is more preferably a $C_7$-$C_9$ alkyl.

According to another preferred embodiment, at least one of $R^1$, $R^2$, $R^3$, and $R^4$ is hydrogen, —C(O)CH$_3$, —OH, Cl, —OCH$_3$, F, or —NO$_2$. In one more preferred embodiment, $R^2$ is —C(O)CH$_3$, —OH, —OCH$_3$, or —Cl. In another more preferred embodiment, $R^3$ is Cl, —OCH$_3$, F, or —OH. In yet another more preferred embodiment, $R^4$ is —OCH$_3$ or —NO$_2$.

According to yet another preferred embodiment, $R^5$ is —C(O)CH$_3$, —OH, H, —CH=CHCH$_3$, —NH$_2$, —NO$_2$, —NHC(O)CH$_3$, —CH=CHCO$_2$H, —C(O)CH$_2$CH$_3$, —C(O)NH$_2$, —C(O)NHCH$_3$, —COOH, —C(O)NHCH$_2$CH$_3$, —C(O)NHCH(CH$_3$)$_2$, —OCH$_3$, —C(CH$_3$)$_2$OH, —C(OH)(CH$_3$)$_2$, or —CH(OH)CH$_3$.

According to yet another preferred embodiment, $R^6$ is a linear $C_1$-$C_{12}$ alkylene. More preferably, $R^6$ is —(CH$_2$)$_n$—, where n is an integer from 1 to 10.

According to yet another preferred embodiment, $R^4$ and $R^5$ are not alkyl or halogen.

According to yet another preferred embodiment, $R^7$ is para-phenylene or a bond.

According to yet another preferred embodiment, $R^6$ is —CH$_2$— and $R^7$ is phenylene and, more preferably para-phenylene. More preferably, at least one of $R^1$, $R^2$, $R^3$, and $R^4$ is hydrogen. More preferably, $R^5$ is —C(O)CH$_3$, —OH or —C(CH$_3$)$_2$OH.

According to yet another preferred embodiment, $R^7$ is a bond, $R^5$ is —OH, and $R^1$, $R^2$, $R^3$, and $R^4$ are hydrogen. $R^6$ is preferably $C_4$-$C_{12}$ alkylene and, more preferably, $C_4$-$C_9$ alkylene.

According to yet another preferred embodiment, $R^7$ is a bond, $R^5$ is —OH, and at least one of $R^1$, $R^2$, $R^3$, and $R^4$ is not hydrogen. $R^6$ is preferably $C_1$-$C_{12}$ alkylene, more preferably $C_5$-$C_{12}$ alkylene, and most preferably $C_5$-$C_9$ alkylene.

According to yet another preferred embodiment, $R^7$ is a bond, $R^5$ is —C(O)CH$_3$, and $R^1$, $R^2$, $R^3$, and $R^4$ are hydrogen. $R^6$ is preferably $C_1$-$C_{12}$ alkylene, more preferably $C_3$-$C_{12}$ alkylene, and most preferably $C_3$-$C_7$ alkylene.

According to yet another preferred embodiment, $R^7$ is a bond and $R^1$, $R^2$, $R^3$, $R^4$ and $R^5$ are hydrogen. Preferably, $R^6$ is $C_7$-$C_8$ alkylene.

According to yet another preferred embodiment, $R^7$ is a bond, $R^5$ is hydrogen, and at least one $R^1$, $R^2$, $R^3$, and $R^4$ are not hydrogen. $R^6$ is preferably $C_1$-$C_{12}$ alkylene, more preferably $C_4$-$C_9$ alkylene, and most preferably $C_7$-$C_8$ alkylene.

According to yet another preferred embodiment, $R^2$ is —OH. More preferably, $R^7$ is a bond and $R^5$ is hydrogen. Preferably, $R^6$ is $C_1$-$C_{12}$ alkylene, more preferably $C_3$-$C_9$ alkylene, and most preferably $C_7$ alkylene.

According to yet another preferred embodiment, $R^3$ is —OH. More preferably, $R^7$ is a bond and $R^5$ is hydrogen. $R^6$ is preferably $C_1$-$C_{12}$ alkylene, more preferably $C_3$-$C_9$ alkylene, and most preferably $C_7$ alkylene.

Other suitable delivery agents include those having the following structure and pharmaceutically acceptable salts thereof:

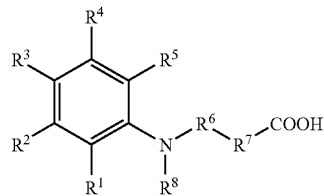

Formula (6)

wherein:
$R^1$, $R^2$, $R^3$, and $R^4$ are independently H, —OH, halogen, —OCH$_3$, —NR$^{10}$R$^{11}$ or —N$^+$R$^{10}$R$^{11}$R$^{12}$ (R$^{13}$)$^-$;
$R^5$ is H, —OH, —NO$_2$, —NR$^{14}$R$^{15}$, —N$^+$R$^{14}$R$^{15}$R$^{16}$ (R$^{13}$)$^-$, amide, $C_1$-$C_{12}$ alkoxy, $C_1$-$C_{12}$ alkyl, $C_2$-$C_{12}$ alkenyl, carbamate, carbonate, urea, or —C(O)R$^{18}$;
$R^5$ is optionally substituted with —OH, —SH, or —COOH;
$R^5$ is optionally interrupted by O, N, S, or —C(O)—;
$R^6$ is a $C_1$-$C_{12}$ alkylene, $C_1$-$C_{12}$ alkenylene, or arylene;
$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^9$;
$R^6$ is optionally interrupted by O or N;
$R^7$ is a bond or arylene;
$R^7$ is optionally substituted with —OH, halogen, —C(O)CH$_3$, —NR$^{10}$R$^{11}$ or —N$^+$R$^{10}$R$^{11}$R$^{12}$ (R$^{13}$)$^-$;
$R^8$ is H or $C_1$-$C_4$ alkyl;
$R^9$ is H, $C_1$-$C_4$ alkyl, or $C_2$-$C_4$ alkenyl;
$R^{10}$, $R^{11}$, and $R^{12}$ are independently H or $C_1$-$C_{10}$ alkyl;
$R^{13}$ is a halide, hydroxide, sulfate, tetrafluoroborate, or phosphate;
$R^{14}$, $R^{15}$, and $R^{16}$ are independently H, $C_1$-$C_{10}$ alkyl, $C_2$-$C_{12}$ alkenyl, O, or —C(O)R$^{17}$;
$R^{17}$ is —OH, $C_1$-$C_{10}$ alkyl, or $C_2$-$C_{12}$ alkenyl; and
$R^{18}$ is —OH, $C_1$-$C_6$ alkyl, —NR$^{14}$R$^{15}$, —N$^+$R$^{14}$R$^{15}$R$^{16}$ (R$^{13}$)$^-$.

According to one embodiment, when $R^5$ is OCH$_3$ then $R^6$ is $C_1$-$C_8$ or $C_{10}$-$C_{12}$ alkyl.

According to a preferred embodiment, $R^5$ is not —OCH$_3$. More preferably, $R^5$ is not alkoxy.

According to another preferred embodiment, $R^1$, $R^2$, $R^3$, and $R^4$ are hydrogen, $R^5$ is —COOH, —C(O)NH$_2$, —C(O)CH$_3$, or —NO$_2$, $R^6$ is —(CH$_2$)$_7$—, and $R^7$ is a bond.

According to yet another preferred embodiment, $R^1$, $R^2$, $R^3$, and $R^4$ are hydrogen, $R^5$ is —C(O)NH$_2$, $R^6$ is —CH$_2$—, and $R^7$ is a para-phenylene.

According to one embodiment, the delivery agents of formula (6) have the formula:

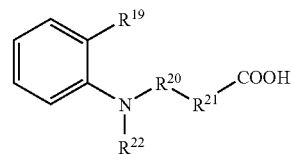

Formula (7)

wherein:
$R^{19}$ is —NO$_2$ or —C(O)R$^{23}$;
$R^{20}$ is a $C_1$-$C_{12}$ alkylene or $C_1$-$C_{12}$ alkenylene;
$R^{21}$ is a bond or arylene;
$R^{22}$ is H or $C_1$-$C_4$ alkyl; and
$R^{23}$ is —OH, $C_1$-$C_6$ alkyl, or —NH$_2$.

Delivery agent compounds of the present invention include compounds as shown below and pharmaceutically acceptable salts thereof:

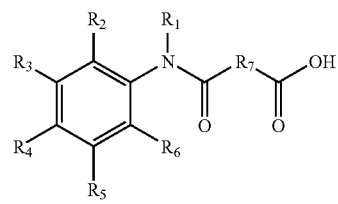

Formula (8)

wherein:
$R_1$ is —(CH$_2$)$_m$—R$_8$, wherein m=0 or 1;
$R_2$-$R_6$ are independently selected from hydrogen, hydroxyl, halogen, $C_1$-$C_4$ alkyl, $C_2$-$C_4$ alkenyl, $C_2$-$C_4$ alkynyl, $C_1$-$C_4$ alkoxy, and cyano;
$R_7$ is selected from $C_1$-$C_{10}$ alkyl, $C_2$-$C_{10}$ alkenyl, and $C_2$-$C_{10}$ alkynyl;
$R_8$ is selected from cyclopentyl, cyclohexyl and phenyl, wherein when $R_8$ is a phenyl, m=1; and
$R_8$ is optionally substituted with $C_1$-$C_4$ alkyl, $C_1$-$C_4$ alkoxy, halogen or hydroxyl, or a combination thereof.

Other delivery agent compounds of the present invention include those of the formula:

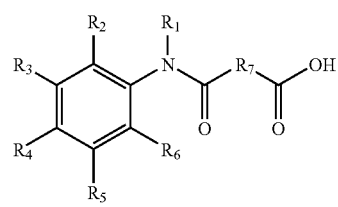

Formual (9)

and pharmaceutically acceptable salts thereof, wherein:
$R_1$ is a $C_1$-$C_6$ alkyl, or $C_2$-$C_6$ alkenyl,
$R_2$-$R_6$ are independently chosen from the group consisting of hydrogen, hydroxyl, halogen, $C_1$-$C_4$ alkyl, $C_2$-$C_4$ alkenyl, $C_2$-$C_4$ alkynyl, $C_1$-$C_4$ alkoxy, and cyano, and
$R_7$ is selected from the group consisting of $C_1$-$C_{10}$ alkyl, $C_2$-$C_{10}$ alkenyl, and $C_2$-$C_{10}$ alkynyl.

Other delivery agent compounds of the present invention include those of the formula:

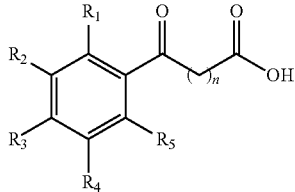

Formula (10)

and pharmaceutically acceptable salts thereof, wherein
n=1 to 9, and
$R_1$ to $R_5$ are independently hydrogen, $C_1$ to $C_4$ alkyl, $C_1$ to $C_4$ alkoxy, $C_2$ to $C_4$ alkenyl, halogen, hydroxyl, —NH—C(O)—CH$_3$, or —O—C$_6$H$_5$.

Other delivery agent compounds of the present invention include those of the formula:

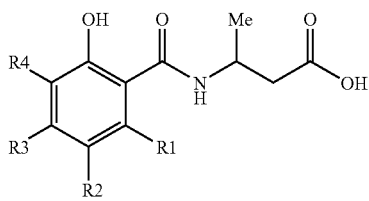

Formula (11)

and pharmaceutically acceptable salts thereof, wherein
$R_1$ to $R_4$ are independently hydrogen, $C_1$ to $C_4$ alkyl, $C_2$ to $C_4$ alkenyl, halogen, $C_1$ to $C_4$ alkoxy, or hydroxyl.

Other delivery agent compounds of the present invention include those of the formula:

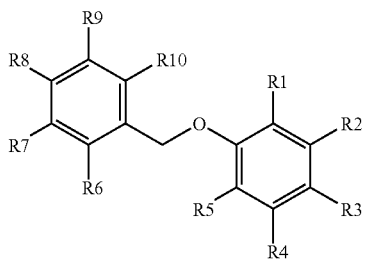

Formula (12)

and pharmaceutically acceptable salts thereof, wherein
one of R1 to R5 has the generic structure —(CH2)$_n$—COOH where n=0-6; and
the remaining four members of $R_1$ to $R_5$ are independently hydrogen, $C_1$ to $C_4$ alkyl, $C_2$ to $C_4$ alkenyl, halogen, $C_1$ to $C_4$ alkoxy, or hydroxyl; and
$R_6$-$R_{10}$ are independently hydrogen, $C_1$ to $C_4$ alkyl, $C_2$ to $C_4$ alkenyl, halogen, $C_1$ to $C_4$ alkoxy, or hydroxyl.

Other delivery agent compounds of the present invention include those of the formula:

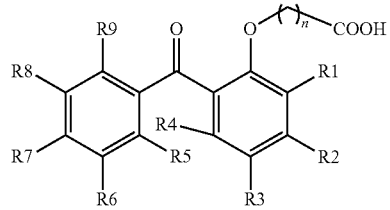

Formula (13)

and pharmaceutically acceptable salts thereof, wherein
n=1 to 9; and
$R_1$ to $R_9$ are independently hydrogen, $C_1$ to $C_4$ alkyl, $C_2$ to $C_4$ alkenyl, halogen, $C_1$ to $C_4$ alkoxy, or hydroxyl.

Other delivery agent compounds of the present invention include those of the formula:

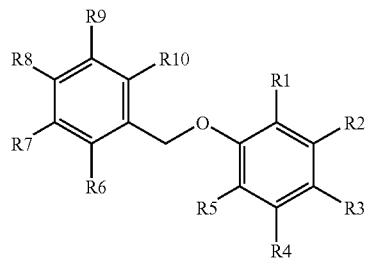

Formula (14)

and pharmaceutically acceptable salts thereof, wherein
$R_1$-$R_5$ are independently hydrogen, $C_1$ to $C_4$ alkyl, $C_2$ to $C_4$ alkenyl, halogen, $C_1$ to $C_4$ alkoxy, hydroxyl, or —O—(CH2)n—COOH (where n is 1 to 12);
at least one of $R_1$ to $R_5$ has the generic structure —O—(CH2)$_n$—COOH where n=1-12; and
$R_6$-$R_{10}$ are independently hydrogen, $C_1$ to $C_4$ alkyl, $C_2$ to $C_4$ alkenyl, halogen, $C_1$ to $C_4$ alkoxy, or hydroxyl. International Application Nos. PCT/US2005/017339 and PCT/US2005/017309, filed May 16, 2005 and their priority documents, U.S. Provisional Application Nos. 60/576,088, filed Jun. 1, 2004, U.S. Provisional Application No. 60/576,397, filed Jun. 1, 2004, U.S. Provisional Application No. 60/576,105, filed Jun. 1, 2004, U.S. Provisional Application No. 60/571,090, filed May 14, 2004, U.S. Provisional Application No. 60/571,092, filed May 14, 2004, U.S. Provisional Application No. 60/571,195, filed May 14, 2004, U.S. Provisional Application No. 60/571,194, filed May 14, 2004, U.S. Provisional Application No. 60/571,093, filed May 14, 2004, U.S. Provisional Application No. 60/571,055, filed May 14, 2004, U.S. Provisional Application No. 60/571,151, filed May 14, 2004, U.S. Provisional Application No. 60/571,315, filed May 14, 2004, U.S. Provisional Application No. 60/571,144, filed May 14, 2004, and U.S. Provisional Application 60/571,089, filed May 14, 2004, are hereby incorporated by reference in their entirety.

Preferred delivery agents include, but are not limited to, 8-(4-Hydroxyphenoxy)octanoic acid (including its monosodium salt), NAC (including SNAC), NAD (including SNAD), 5-CNAC, 4-MOAC, 4-CNAB, and pharmaceutically acceptable salts thereof. In one preferred embodiment, the delivery agent is SNAC. In one embodiment, the delivery agent is a di-sodium salt of NAC. In another embodiment, the delivery agent is SNAD.

Other suitable delivery agents of the present invention are described in U.S. Pat. Nos. 6,846,844, 6,699,467, 6,663,898, 6,693,208, 6,693,073, 6,693,898, 6,663,887, 6,646,162, 6,642,411, 6,627,228, 6,623,731, 6,610,329, 6,558,706, 6,525,020, 6,461,643, 6,461,545, 6,440,929, 6,428,780, 6,413,550, 6,399,798, 6,395,774, 6,391,303, 6,384,278, 6,375,983, 6,358,504, 6,346,242, 6,344,213, 6,331,318, 6,313,088, 6,245,359, 6,242,495, 6,221,367, 6,180,140, 6,100,298, 6,100,285, 6,099,856, 6,090,958, 6,084,112, 6,071,510, 6,060,513, 6,051,561, 6,051,258, 6,001,347, 5,990,166, 5,989,539, 5,976,569, 5,972,387, 5,965,121, 5,962,710, 5,958,451, 5,955,503, 5,939,381, 5,935,601, 5,879,681, 5,876,710, 5,866,536, 5,863,944, 5,840,340, 5,824,345, 5,820,881, 5,811,127, 5,804,688, 5,792,451, 5,776,888, 5,773,647, 5,766,633, 5,750,147, 5,714,167, 5,709,861, 5,693,338, 5,667,806, 5,650,386, 5,643,957, 5,629,020, 5,601,846, 5,578,323, 5,541,155, 5,540,939, 5,451,410, 5,447,728, 5,443,841, and 5,401,516. Delivery agents of the present invention are also described in U.S. Published Application Nos. 20050009748, 20040110839, 20040106825, 20040068013, 20040062773, 20040022856, 20030235612, 20030232085, 20030225300, 20030198658, 20030133953, 20030078302, 20030072740, 20030045579, 20030012817, 20030008900, 20020155993, 20020127202, 20020120009, 20020119910, 20020102286, 20020065255, 20020052422, 20020040061, 20020028250, 20020013497, 20020001591, 20010039258, and 20010003001. Delivery agents of the present invention are also described in International Publication Nos. WO 2005/020925, 2004/104018, 2004/080401, WO 2004062587, WO 2003/057650, WO 2003/057170, WO 2003/045331, WO 2003/045306, WO 2003/026582, WO 2002/100338, WO 2002/070438, WO 2002/069937, WO 02/20466, WO 02/19969, WO 02/16309, WO 02/15959, WO 02/02509, WO 01/92206, WO 01/70219, WO 01/51454, WO 01/44199, WO 01/34114, WO 01/32596, WO 01/32130, WO 00/07979, WO 00/06534, WO 00/06184, WO 00/59863, WO 00/59480, WO 00/50386, WO 00/48589, WO 00/47188, WO 00/46182, WO 00/40203, WO 99/16427, WO 98/50341, WO 98/49135, WO 98/34632, WO 98/25589, WO 98/21951, WO 97/47288, WO 97/31938, WO 97/10197, WO 96/40076, WO 96/40070, WO 96/39835, WO 96/33699, WO 96/30036, WO 96/21464, WO 96/12475, and WO 9612474. Each of the above listed U.S. patents and U.S. and International published applications are herein incorporated by reference.

The delivery agent compounds depicted as carboxylic acids may be in the form of the carboxylic acid or salts thereof. Suitable salts include, but are not limited to, organic and inorganic salts, for example alkali-metal salts, such as sodium (e.g., monosodium and disodium salts), potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

The delivery agent compounds depicted as amines may be in the form of the free amine or salts thereof. Suitable salts include, but are not limited to, organic and inorganic salts, for example sodium salts, sulfate salts, hydrochloride salts, phosphate salts, fluoride salts, carbonate salts, tartrate salts, oxalates, oxides, formates, acetate or citrate.

Salts of the delivery agent compounds of the present invention may be prepared by methods known in the art. For example, sodium salts may be prepared by dissolving the delivery agent compound in ethanol and adding aqueous sodium hydroxide.

Where the delivery agent has an amine moiety and a carboxylic acid moiety, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids. One or more of the amino acids or peptide units may be acylated or sulfonated.

The delivery agent may contain a polymer conjugated to it such as described in International Publication No. WO 03/045306. For example, the delivery agent and polymer may be conjugated by a linkage group selected from the group consisting of —NHC(O)NH—, —C(O)NH—, —NHC(O), —OOC—, —COO—, —NHC(O)O—, —OC(O)NH—, —CH$_2$NH—NHCH$_2$—, —CH$_2$NHC(O)O—, —OC(O)NHCH$_2$—, —CH$_2$NHCOCH$_2$O—, —OCH$_2$C(O)NHCH$_2$—, —NHC(O)CH$_2$O—, —OCH$_2$C(O) NH—, —NH—, —O—, and carbon-carbon bond. In one embodiment, the polymeric delivery agent is not a polypeptide or polyamino acid. The polymer may be any polymer including, but not limited to, alternating copolymers, block copolymers and random copolymers, which are safe for use in mammals.

Preferred polymers include, but are not limited to, polyethylene; polyacrylates; polymethacrylates; poly (oxyethylene); poly (propylene); polypropylene glycol; polyethylene glycol (PEG); and derivatives thereof and combinations thereof. The molecular weight of the polymer typically ranges from about 100 to about 200,000 daltons. The molecular weight of the polymer preferably ranges from about 200 to about 10,000 daltons. In one embodiment, the molecular weight of the polymer ranges from about 200 to about 600 daltons and more preferably ranges from about 300 to about 550 daltons.

The compounds described herein may be derived from amino acids and can be readily prepared from amino acids by methods within the skill of those in the art, such as those described in International Publication Nos. WO 96/30036, WO 97/36480, WO 00/06534, WO 00/46812, WO 00/50386, WO 00/59863, WO 01/32596, WO 01/92206, and WO 00/07979 and U.S. Pat. Nos. 5,643,957, 5,650,386, and 5,866,536, all of which are incorporated by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art. With regard to protecting groups, reference is made to T. W. Greene, *Protecting Groups in Organic Synthesis*, Wiley, New York (1981), the disclosure of which is hereby incorporated herein by reference.

The delivery agent compound may be purified by recrystallization or by fractionation on one or more solid chromatographic supports, alone or linked in tandem. Suitable recrystallization solvent systems include, but are not limited to, acetonitrile, methanol, ethanol, ethyl acetate, heptane, water, tetrahydrofuran, and combinations thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Human Growth Hormone (hGH) Component

Any form of human growth hormone (hGH) known in the art may be used. Preferably, the hGH component is non-immunogenic. Suitable forms include, but are not limited to, natural or recombinant hGH. Examples of suitable recombinant hGH include, but are not limited to, commercially available recombinant hGH comprising 191 amino acids such as Nutropin® (commercially available from Genentech, South San Francisco, Calif.), recombinant met-hGH comprising 192 amino acids such as Protropin® (commercially available from Genentech, South San Francisco, Calif.), as well as naturally occurring splice variants such as those disclosed in U.S. Pat. No. 6,566,328 (which is hereby incorporated by reference). Alternatively, the hGH component can be any polypeptide, protein, protein fragment, or modified fragment of the endogenous 191 amino acid hGH or the 192 amino acid met-hGH, i.e. hGH-related peptides and hGH analogs and variants such as those disclosed in U.S. Pat. No. 6,780,613 (which is hereby incorporated by reference) that are capable of mimicking the activity of endogenous human growth hormone in stimulating tissue growth.

According to one embodiment, the hGH component is a recombinant hGH comprising 191 amino acids, having a molecular weight of about 22,125 Daltons, such as Nutropin® (commercially available from Genentech, South San Francisco, Calif.).

The hGH component can be a single type of hGH or a combination of two or more types of hGH. The hGH components are generally commercially available or can be obtained recombinantly such as by the methods described in U.S. Pat. Nos. 4,670,393, 5,424,199, 5,633,352 and 5,795,745, which are hereby incorporated by reference, by peptide synthesis, or by extraction from the human pituitary gland by methods known in the art.

The amount of hGH to be administered is generally a therapeutically effective amount. For example, the amount can be that effective to treat growth hormone deficiency or to stimulate new tissue growth in a subject. This amount may vary with the age, size, sex and condition of the subject to be treated, the nature and severity of the disorder to be treated. The total amount of hGH to be used can be determined by methods known to those skilled in the art. According to one embodiment, from about 0.001 µg/kg to about 10 mg/kg animal body weight, from about 0.01 µg/kg to about 1 or 5 mg/kg body weight or from about 0.1 µg/kg to about 0.5 or 3 mg/kg body weight of the hGH component is administered.

Pharmaceutical Compositions

The pharmaceutical composition of the present invention comprises one or more delivery agents and a hGH component. The delivery agent(s) and hGH component are typically mixed prior to administration to form an administration composition.

The administration composition may be in the form of a liquid dosage form. The solution medium may be water, 25% aqueous propylene glycol, or phosphate buffer. Other dosing vehicles include polyethylene glycol. Dosing solutions may be prepared by mixing a solution of the delivery agent compound with a solution of the hGH component, just prior to administration. Alternately, a solution of the delivery agent (or hGH) may be mixed with the solid form of hGH (or the delivery agent). The delivery agent and hGH may also be mixed as dry powders. The delivery agent compound and hGH can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging from about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the hGH component. Alternately, a solid may be obtained from a solution of the delivery agent compound and the hGH component by methods known in the art, such as freeze-drying (lyophilization), precipitation, crystallization and solid dispersion. Alternatively, the administration can be a semi-solid, in the form of a gel, paste, colloid, gelatin, emulsion, suspension and the like.

Without being bound by any particular theory, applicants believe that there is less dilution and fewer food effects when the human growth hormone component is absorbed buccally.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

Dosage unit forms for buccal administrations may contain ingredients known to facilitate buccal administration. The buccal dosage unit form, for example, may be formulated so as to erode gradually over a predetermined time period and release the human growth hormone component and delivery agent at a constant or substantially constant rate. According to one embodiment, the time period ranges from about 0.5 hours to about 24 hours. A bioerodible (hydrolyzable) polymeric carrier that adheres the dosage form to the buccal mucosa, such as that described in U.S. Published Patent Application No. 2003/0134861 (which is hereby incorporated by reference), can be used, e.g., to provide a sustained release profile. Suitable bioerodible (hydrolyzable) polymeric carriers include, but are not limited to, those which provide a sustained release profile and are compatible with hGH.

According to one embodiment, the polymeric carrier comprises hydrophilic (water-soluble and water-swellable) polymers that adhere to the wet surface of the buccal mucosa. Non-limiting examples of polymeric carriers useful herein include acrylic acid polymers, e.g., those known as "carbomers" (Carbopol®, which may be obtained from B. F. Goodrich is one such polymer). Other suitable polymers include, but are not limited to: hydrolyzed polyvinylalcohol; polyethylene oxides (e.g., Sentry Polyox® water soluble resins, available from Union Carbide of Midland, Mich.); polyacrylates (e.g., Gantrez®, which may be obtained from GAF of Wayne, N.J.); vinyl polymers and copolymers; polyvinylpyrrolidone; dextran; guar gum; pectins; starches; and cellulosic polymers such as hydroxypropyl methylcellulose (e.g., Methocel®, which may be obtained from the Dow Chemical Company of Midland, Mich.), hydroxypropyl cellulose (e.g., Klucel®, which may also be obtained from Dow), hydroxypropyl cellulose ethers (see, e.g., U.S. Pat. No. 4,704,285), hydroxyethyl cellulose, carboxymethyl cellulose, sodium carboxymethyl cellulose, methyl cellulose, ethyl cellulose, cellulose acetate phthalate, cellulose acetate butyrate, and the like.

Other components may also be incorporated into the buccal dosage forms described herein. The additional components include, but are not limited to, disintegrants, diluents, binders, lubricants, flavoring, colorants, preservatives, and the like. Non-limiting examples of disintegrants are cross-linked polyvinylpyrrolidones, such as crospovidone (e.g., Polyplasdone® XL, which may be obtained from GAF), cross-linked carboxylic methylcelluloses, such as croscarmelose (e.g., Ac-di-sol®, which may be obtained from FMC Corporation of Philadelphia, Pa.), alginic acid, and sodium carboxymethyl starches (e.g., Explotab®, which may be obtained from Edward Medell Co., Inc.), methylcellulose, agar bentonite and alginic acid. Suitable diluents include, but are not limited to, those which are generally useful in pharmaceutical formulations prepared using compression techniques, e.g., dicalcium phosphate dihydrate (e.g., Di-Tab®, which may be obtained from Stauffer), sugars that have been processed by cocrystallization with dextrin (e.g., co-crystallized sucrose and dextrin such as Di-Pakg, which may be obtained from Amstar), lactone, calcium phosphate, cellulose, kaolin, mannitol, sodium chloride, dry starch, powdered sugar and the like. Suitable binders include, but are not limited to, those that enhance adhesion. Non-limiting examples of such binders are starch, gelatin and sugars such as sucrose, dextrose, molasses, and lactose. Non-limiting examples of lubricants include, but are not limited to, stearates (e.g., magnesium stearate) and stearic acid.

Preferred sublingual dosage forms include sublingual tablets, creams, ointments and pastes. The tablet, cream, ointment or paste for sublingual delivery comprises a therapeutically effective amount of hGH and one or more conventional nontoxic carriers suitable for sublingual drug administration. The sublingual dosage forms of the present invention can be manufactured using conventional processes. The sublingual dosage unit is fabricated to disintegrate rapidly. The time period for complete disintegration of the dosage unit is typically in the range of from about 10 seconds to about 30 minutes, and optimally is less than about 5 minutes.

Other components may also be incorporated into the sublingual dosage forms described herein. The additional components include, but are not limited to, binders, disintegrators, wetting agents, lubricants, and the like. Examples of binders that may be used include water, ethanol, polyvinyl pyrrolidone, and starch solution gelatin solution. Suitable disintegrators include, but are not limited to, dry starch, calcium carbonate, polyoxyethylene sorbitan fatty acid esters, sodium lauryl sulfate, stearic monoglyceride, and lactose. Wefting agents, if used, include glycerin, and starches. Suitable lubricants include but are not limited to, stearates and polyethylene glycol. Additional components that may be incorporated into sublingual dosage forms include those known in the art; such as those described in *Remington's, The Science and Practice of Pharmacy*, (Gennaro, A. R., ed., 20th edition, 2003, Mack Pub. Co.) which is herein incorporated by reference.

One or more of a solvent, an optional cosolvent, a hydrogel, and an oral mucosal membrane transport enhancing agent, such as those described in U.S. Pat. No. 5,284,657 (which is hereby incorporated by reference), may be included in the dosage unit form for buccal administration. The solvent may comprise from about 50 percent w/v to about 95 percent w/v or from about 55 percent w/v to about 80 percent w/v of a carrier of a non-toxic alcohol. Suitable non-toxic alcohols include, but are not limited to, ethanol, isopropanol, stearyl alcohol, propylene glycol, and polyethylene glycol (e.g., those having a molecular weight of up to about 650 daltons). Non-toxic alcohols for use in pharmaceutical formulations are well known in the art (cf., for example, *Handbook of Pharmaceutical Excipients*, published by the American Pharmaceutical Association and The Pharmaceutical Society of Great Britain (1986), which is hereby incorporated by reference in its entirety).

The cosolvent may be selected from water or a pharmaceutically acceptable oil. Suitable oils for use in the unit dosage form of this invention include mineral oil, Neobee™ oil, olive oil, sunflower oil, corn oil, peanut oil and the like. Hydrogels suitable for use in the dosage unit form include hydroxypropyl cellulose, hydroxypropyl methyl cellulose, sodium carboxymethylcellulose (CMC), polyacrylic acid, and poly(methyl methacrylic acid).

Typically, the oral mucosal membrane transport enhancing agent facilitates the absorption of the therapeutic agent (e.g., human growth hormone) across the mucosal tissues in the oral cavity and directly into the blood stream of the subject. Suitable tissue transport enhancing agents include, but are not limited to, pharmaceutically acceptable and non-toxic essential oils, volatile oils, inorganic acids, and organic acids.

Essential or volatile oils which may be employed in the compositions include, but are not limited to, peppermint oil, spearmint oil, menthol, pepper oil, eucalyptus oil, cinnamon oil, ginger oil, fennel oil, and dill oil. The essential or volatile oil, when employed as the oral mucosal membrane transport enhancing agent in the dosage unit form may be present in a concentration ranging between about 0.5 percent w/v and 50 percent w/v of the carrier.

Suitable inorganic and organic acids include, but are not limited to, hydrochloric acid, phosphoric acid, aromatic and aliphatic monocarboxylic or dicarboxylic acids of from two to thirty carbon atoms such as acetic acid, citric acid, lactic acid, oleic acid, linoleic acid, lauric acid, palmitic acid, benzoic acid, and salicylic acid. As used in this paragraph, the term "aromatic" carboxylic acid refers to any acid which contains the 6-membered carbocyclic ring system characteristic of benzene, and the term "aliphatic" carboxylic acid refers to any acid which contains a straight-chain or branched chain saturated or unsaturated hydrocarbon backbone.

Liquid compositions for buccal administration can be formulated into a liquid spray, a liquid drop, a gel or a paste. The desired consistency can be achieved by including in the liquid composition one or more hydrogels, substances that absorb water and produce gels of varying viscosity. Hydrogels suitable for use in pharmaceutical preparations include those known well known in the art, such as those described in *Handbook of Pharmaceutical Excipients*, supra, and *Handbook of Water-Soluble Gums and Resins*, ed. by R. L. Davidson, McGraw-Hill Book Co., New York, N.Y. (1980) (both of which are hereby incorporated by reference).

Suitable hydrogels for use in the compositions of this invention include hydroxypropyl cellulose, hydroxypropyl methyl cellulose, sodium carboxymethyl cellulose, polyacrylic acid, poly(methyl methacrylic acid) (PMMA). Preferred hydrogels are cellulose ethers such as hydroxyalkyl-cellulose (e.g., hydroxypropyl cellulose) and hydroxyalkylalkyl-cellulose compounds. Hydroxypropyl cellulose is commercially available in a wide range of viscosity grades sold under the tradename Klucel™ (Hercules, Ltd., London, England). The concentration of the hydroxyalkyl-cellulose is dependent upon the particular viscosity grade used and the desired viscosity of the liquid composition. For example, where the desired viscosity is less than about 1000 centipoise (cps), hydroxypropyl cellulose having an average molecular weight of about 60,000 daltons (i.e., Klucel EF™) can be used. Where the desired viscosity is from about 1000 to about 2500 cps, higher viscosity grades of hydroxypropyl cellulose can be used (e.g., Klucel LF™ and Lucel GF™).

The dosage unit form for buccal administration may also include collagen, a water soluble additive, and/or other pharmaceutical additives, such as those described in U.S. Pat. No. 5,496,559. Collagen includes, for example, atelocollagen which is derived from a natural resource, and which is free of a telopeptide which is an antigenic portion of collagen; chemically modified atelocollagen; and naturally-occurring collagen. The collagen which has been chemically derived from the atelocollagen includes, for example, a succinylated collagen and a methylated collagen. The naturally-occurring collagen includes, for example, a collagen from a skin of bovine, a chorda of bovine, a bowel of porcine and sheep, and a human placenta. The collagen can contain a buffer, such as phosphate buffer, citrate buffer, and acetate buffer, and/or a stabilizer. Water soluble additives include for example, proteins, glycoproteins, amino acids, polyamino acids, peptides, saccharides, water-soluble polysaccharides, or a combination thereof. Proteins include, for example, gelatin and albumin. Glycoproteins include, for example, globulin. Amino acids include, for example, aspartic acid, arginine, glycine, and leucine. Polyamino acids and peptides include, for example, polyalanine, polyglycine, sodium polygultamate, sodium polyaspartate, polylysine, and polyleucine. Saccharides, polysaccharides, and water-soluble polysaccharides include, for example, fructose, sucrose, lactose, dextran, cyclodextran, mannitol, and sorbitol. A stabilizer includes one which is used for the proteinaceous physiologically active substances, such as albumin, gelatin, mannitol, and trehalose. Suitable preservatives include, but are not limited to, p-hydroxybenzoates, sorbic acid, and salkylic acid. Suitable buffers include, but are not limited to, citrate buffer, acetate buffer, and phosphate buffer. Suitable sweeteners include, but are not limited to, mannitol, glucose, maltose, starch, and lactose. Suitable flavors include, but are not limited to, aspartic acid, citric acid, and lactic acid. Suitable binder include, but are not limited to, methylcellulose, ethylcellulose, and carboxy methyl cellulose. Suitable suspending agents include, but are not limited to, Tween 20 and Tween 80. Suitable disintegrators include, but are not limited to, glycerol and starch.

Dosage unit forms for buccal administration may be in the form of a hard candy (e.g. lollipops and mints) or a film, e.g., a slow dissolving film or a fast dissolving film (such as that described in U.S. Pat. No. 6,596,298, which is hereby incorporated by reference). Such films can be prepared by including a film forming agent in the dosage unit form. Suitable film forming agents include, but are not limited to, those described in U.S. Pat. No. 6,596,298 (e.g., pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. According to one embodiment, the concentration of film forming agent in the dosage unit form ranges from about 0.01 to about 99 wt %, from about 30 to about 80 wt %, from about 45 to about 70 wt %, or from about 60 to about 65 wt % (based upon 100% total weight of the film). Administration compositions can also take the form of a pouch that can be placed next to the cheek, or between the lower teeth and lip, similar to smoke-less tobacco products.

The compounds and compositions of the subject invention are useful for administering biologically or chemically active agents to any animals, including but not limited to insects, birds such as chickens; fish, reptiles, mammals, such as rodents, cows, pigs, dogs, cats, primates, and particularly humans.

EXAMPLES

The following example illustrates the invention without limitation. All parts are given by weight unless otherwise indicated.

Example 1

Buccal Administration of Human Growth Hormone (hGH)

Human growth hormone (hGH) and the disodium salt of 8-(4-Hydroxyphenoxy)octanoic acid (delivery agent) was administered to Beagle dogs orally in solid and liquid dosage forms and bucally with in solid and gel forms. The dose of hGH was either 3 or 1.5 mg/kg body weight, the dose of delivery agent was either 50 or 25 mg/kg body weight, as indicated below in Table 1.

A stock solution of human recombinant hGH was prepared by dissolving recombinant hGH (native 191 amino acid form) (available from Eli Lilly and Company, Indianapolis, Ind.) in deionized water to a concentration of 60 mg/ml. A stock solution of delivery agent was prepared by dissolving the delivery agent in deionized water to yield a concentration of 1000 mg/ml. The pH of the resulting delivery agent solution was adjusted to between 7.5 and 8.5.

A liquid dosage form was prepared by mixing the stock solutions of hGH and delivery agent to achieve 3 mg/kg of hGH and 50 mg/kg of Delivery Agent. A solid dosage form was prepared by compacting the mixture of pre-weighed hGH and delivery agent in a tablet-forming mold at 1000 psi. A gel dosage form was prepared by introducing 3% (w/w) Klucel® (hydroxypropyl cellulose) to the hGH and delivery agent solutions.

The resulting dosage forms for use in the present example are further described in Table 1, below:

TABLE 1

| | | Dosage Forms | | | |
|---|---|---|---|---|---|
| Trial | Dose | Delivery Agent | Delivery Agent Dose (mg/kg) | hGH Dose (mg/kg) | Dosing Route |
| A | Solid | 8-(4-Hydroxyphenoxy)octanoic acid | 50 | 3 | Buccal |
| B | Solid | 8-(4-Hydroxyphenoxy)octanoic acid | 50 | 3 | Oral |

TABLE 1-continued

Dosage Forms

| Trial | Dose | Delivery Agent | Delivery Agent Dose (mg/kg) | hGH Dose (mg/kg) | Dosing Route |
|---|---|---|---|---|---|
| C | Solid | 8-(4-Hydroxyphenoxy)octanoic acid | 50 | 1.5 | Buccal |
| D | Gel | 8-(4-Hydroxyphenoxy)octanoic acid | 50 | 3 | Buccal |
| E | Gel | 8-(4-Hydroxyphenoxy)octanoic acid | 25 | 1.5 | Buccal |
| F | Liquid | 8-(4-Hydroxyphenoxy)octanoic acid | 50 | 3 | Oral |

The dosage forms were administered to beagles who were fasted overnight. Each dog was anesthetized with 0.2 mg/kg of atropine and 0.04 mg/kg of midazolan IV injection. The animal's body temperature, heart beat and breathing rate were monitored frequently. A Teflon IV cannula was secured into the cephalic vein for blood sampling, after the depth of anesthesia was confirmed.

For dosing the sublingual tablet, the animal was anesthetized first as described above. Its mouth was opened, and the tablet was placed under the tongue. A 1 ml of saline solution was added to facilitate the dissolution. The dissolving profile was visually observed by opening its mouth at 10, 30 and 60 minutes. For the gel dosage form, the dosing volume was 0.1 ml/kg of animal, and the gel was placed under the tongue. The animal's jaw was maintained parallels on the surface of a table so that the gel did not leak out through the mouth. The serum concentration of hGH was determined using the rhGH ELISA with a sandwich type enzyme-linked immunosorbent assay.

The detection limit for the present assay is about 2.5 ng/ml of hGH. Typically, a percent deviation of no greater than ±25% from the target concentration at rhGH concentrations of 10 ng/mL or below was used as appropriate.

The individual results for Trials A, C, D and E are respectively set forth in Tables 2-5 below.

TABLE 2

Results for Buccally Administered Solid Dosage Form "Trial A" (50 mg/kg of Delivery Agent, 3 mg/kg of hGH, n = 8)

| Time [min] | Animal 1 | 2 | 3 | 4 | 5 | 6 | 7 | 8 | MEAN [ng/ml] | SD [ng/ml] |
|---|---|---|---|---|---|---|---|---|---|---|
| 0 | 2.5 | 2.5 | 2.5 | 2.5 | 2.5 | 2.5 | 2.5 | 2.5 | 2.5 | 0 |
| 15 | 4.74 | 3.47 | 18.96 | 2.5 | 2.5 | 34.72 | 2.5 | 2.5 | 9.0 | 11.83 |
| 30 | 30.14 | 58.00 | 24.64 | 3.42 | 2.5 | 9.55 | 4.92 | 2.5 | 17.0 | 19.71 |
| 45 | 36.59 | 19.20 | 23.24 | 5.51 | 18.62 | 15.98 | 2.5 | 2.5 | 15.52 | 11.75 |
| 60 | 85.42 | 28.90 | 48.79 | 8.89 | 46.66 | 74.12 | 2.70 | 4.07 | 37.44 | 31.78 |
| 90 | 40.73 | 56.03 | 100 | 37.27 | 56.96 | 58.07 | 7.24 | 13.08 | 46.17 | 29.21 |
| 120 | 24.50 | 57.77 | 100 | 16.75 | 71.21 | 48.93 | 11.42 | 28.08 | 44.83 | 30.52 |
| 150 | 37.54 | 56.50 | 60.16 | 8.03 | 49.16 | 59.70 | 18.27 | 18.62 | 38.5 | 21.01 |
| 180 | 20.77 | 48.30 | 37.06 | 8.97 | 72.77 | 31.66 | 17.73 | 26.74 | 33.00 | 20.12 |

TABLE 3

Results for Buccally Administered Solid Dosage Form "Trial C" (50 mg/kg of Delivery Agent, 1.5 mg/kg of hGH, n = 4)

| Time [min] | Animal 1 | 2 | 3 | 4 | MEAN [ng/ml] | SD [ng/ml] |
|---|---|---|---|---|---|---|
| 0 | 2.5 | 2.5 | 2.5 | 2.5 | 2.5 | 0 |
| 10 | 2.5 | 2.5 | 2.5 | 2.5 | 2.5 | 0 |
| 20 | 2.5 | 2.5 | 2.5 | 2.5 | 2.5 | 0 |
| 45 | 4.16 | 5.69 | 6.56 | 3.04 | 4.86 | 1.57 |
| 60 | 4.54 | 6.62 | 6.37 | 6.71 | 6.06 | 1.02 |
| 75 | 8.57 | 13.34 | 11.46 | 7.41 | 10.20 | 2.70 |
| 90 | 7.18 | 36.75 | 9.26 | 7.62 | 15.20 | 14.39 |
| 120 | 8.45 | 14.16 | 8.67 | 12.57 | 10.96 | 2.85 |
| 150 | 6.95 | 12.10 | 5.84 | 8.06 | 8.24 | 2.73 |
| 180 | 10.79 | 25.40 | 4.86 | 7.65 | 12.18 | 9.14 |
| 210 | 20.27 | 13.18 | 3.75 | 10.13 | 11.83 | 6.86 |
| 240 | 12.92 | 10.0 | 5.57 | 9.74 | 9.56 | 3.02 |

TABLE 4

Results for Bucally Administered Gel Dosage Form "Trial D" (50 mg/kg of Delivery Agent, 3 mg/kg of hGH, n = 4)

| Time [min] | Animal 1 | 2 | 3 | 4 | MEAN [ng/ml] | SD [ng/ml] |
|---|---|---|---|---|---|---|
| 0 | 2.5 | 2.5 | 2.5 | 2.5 | 2.5 | 0 |
| 10 | 4.59 | 3.48 | 17.76 | 4.97 | 7.70 | 3.37 |
| 20 | 5.37 | 14.02 | 6.20 | 18.22 | 10.95 | 3.12 |
| 45 | 13.00 | 12.18 | 8.67 | 12.25 | 11.52 | 0.97 |
| 60 | 19.06 | 36.10 | 15.25 | 15.37 | 21.45 | 4.96 |
| 75 | 14.23 | 40.95 | 11.75 | 11.90 | 19.71 | 7.10 |
| 90 | 15.89 | 50.15 | 18.05 | 16.49 | 25.14 | 8.35 |
| 120 | 18.35 | 46.32 | 11.00 | 13.19 | 22.22 | 8.18 |
| 150 | 19.16 | 51.39 | 8.88 | 13.83 | 23.32 | 9.59 |
| 180 | 18.27 | 30.28 | 20.39 | 9.33 | 19.57 | 4.30 |
| 210 | 14.61 | 14.64 | 8.74 | 18.43 | 14.10 | 2.00 |
| 240 | 16.04 | 10.94 | 9.94 | 8.11 | 11.27 | 1.69672 |

TABLE 5

Results for Buccally Administered Gel Dosage Form "Trial E" (25 mg/kg of Delivery Agent, 1.5 mg/kg of hGH, n = 4)

| Time [min] | Animal 1 | 2 | 3 | 4 | MEAN [ng/ml] | SD [ng/ml] |
|---|---|---|---|---|---|---|
| 0 | 2.5 | 2.5 | 2.5 | 2.5 | 2.5 | 0 |
| 10 | 2.5 | 2.5 | 2.5 | 2.5 | 2.5 | 0 |
| 20 | 5.96 | 2.5 | 6.63 | 2.5 | 4.40 | 2.21 |
| 45 | 14.35 | 8.76 | 24.79 | 7.18 | 13.77 | 7.96 |
| 60 | 14.49 | 10.82 | 11.81 | 4.53 | 10.41 | 4.22 |
| 75 | 13.17 | 10.82 | 13.75 | 9.97 | 11.93 | 1.82 |
| 90 | 39.32 | 19.74 | 82.99 | 11.17 | 38.30 | 32.04 |
| 120 | 17.41 | 24.14 | 18.87 | 16.43 | 19.21 | 3.43 |
| 150 | 10.55 | 8.41 | 12.86 | 8.88 | 10.17 | 2.02 |
| 180 | 5.42 | 4.29 | 9.54 | 5.48 | 6.18 | 2.31 |
| 210 | 2.94 | 3.54 | 15.27 | 5.07 | 6.70 | 5.78 |
| 240 | 2.77 | 4.34 | 6.69 | 3.41 | 4.30 | 1.72 |

Figure 2:
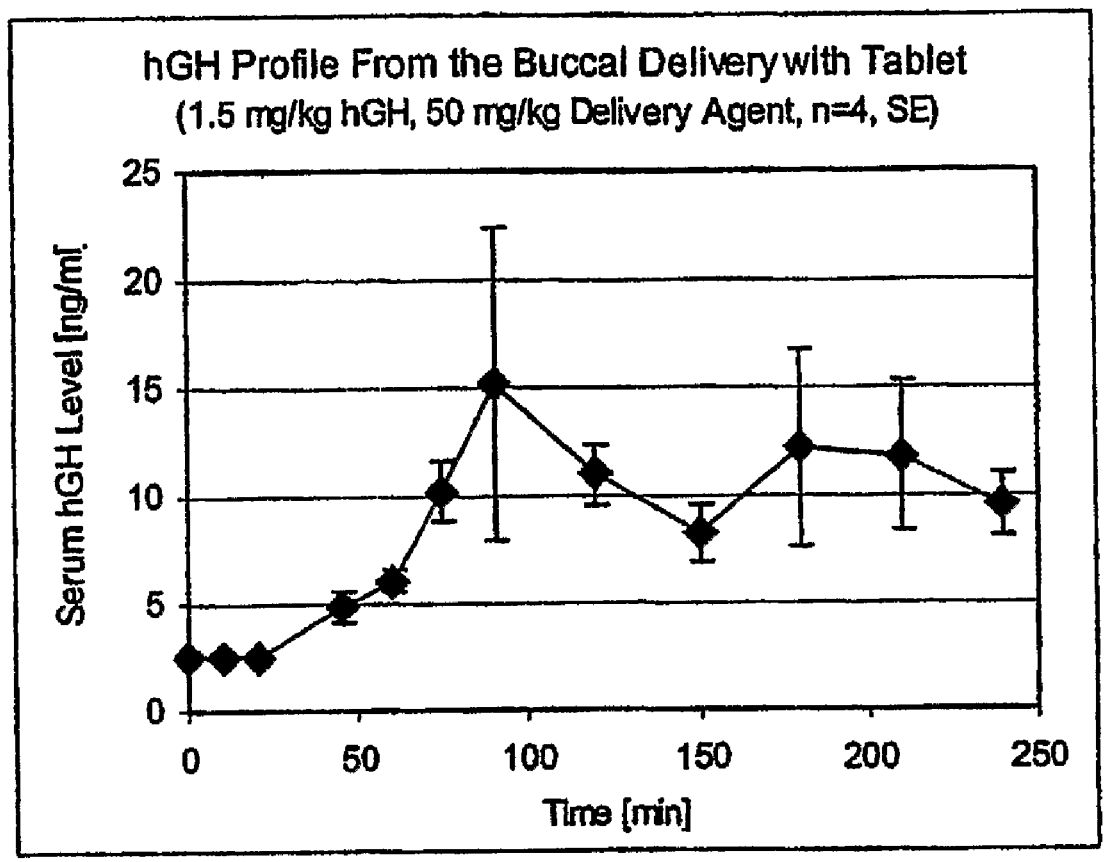
FIG. 2 is a graph of mean human growth hormone (hGH) concentrations over time after buccal administration of a solid dosage form containing 1.5 mg/kg hGH with 50 mg/kg monosodium 8-(4-Hydroxyphenoxy)octanoic acid in beagles.
Figure 3:
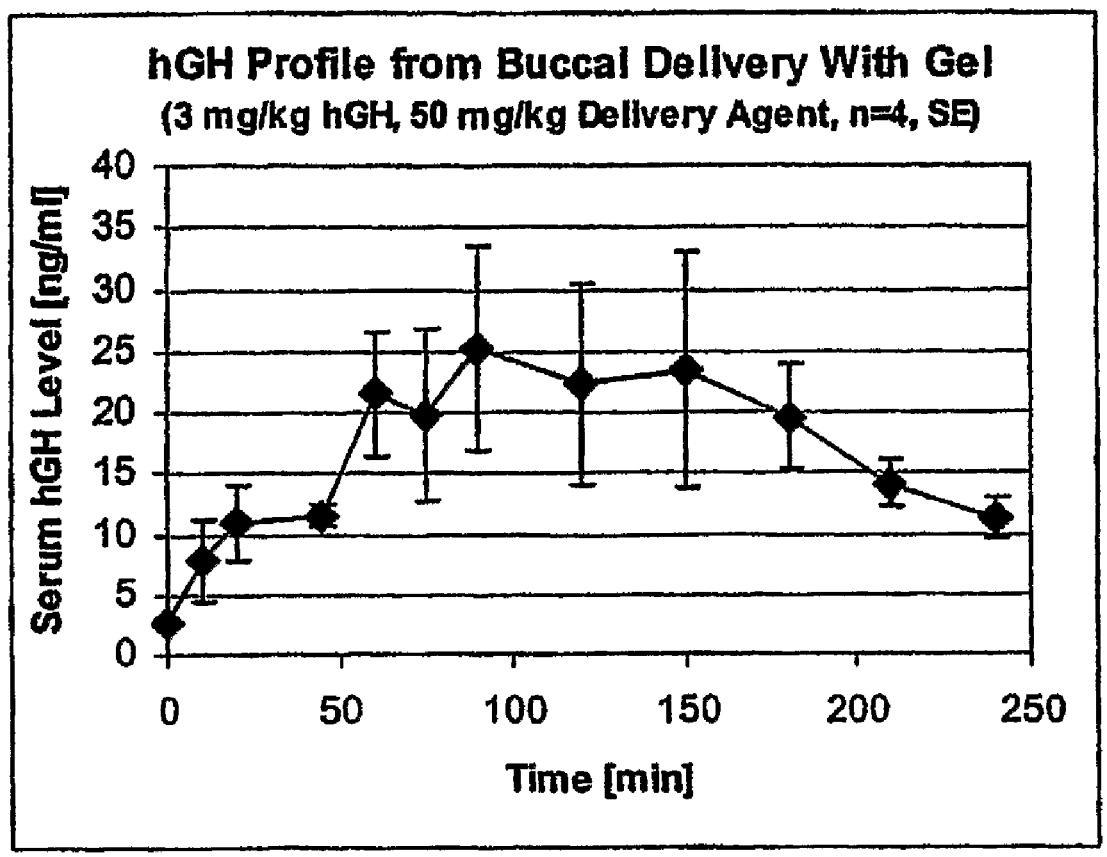
FIG. 3 is a graph of mean human growth hormone (hGH) concentrations over time after buccal administration of a gel dosage form containing 3.0 mg/kg hGH with 50 mg/kg monosodium 8-(4-Hydroxyphenoxy)octanoic acid in beagles.
Figure 4:
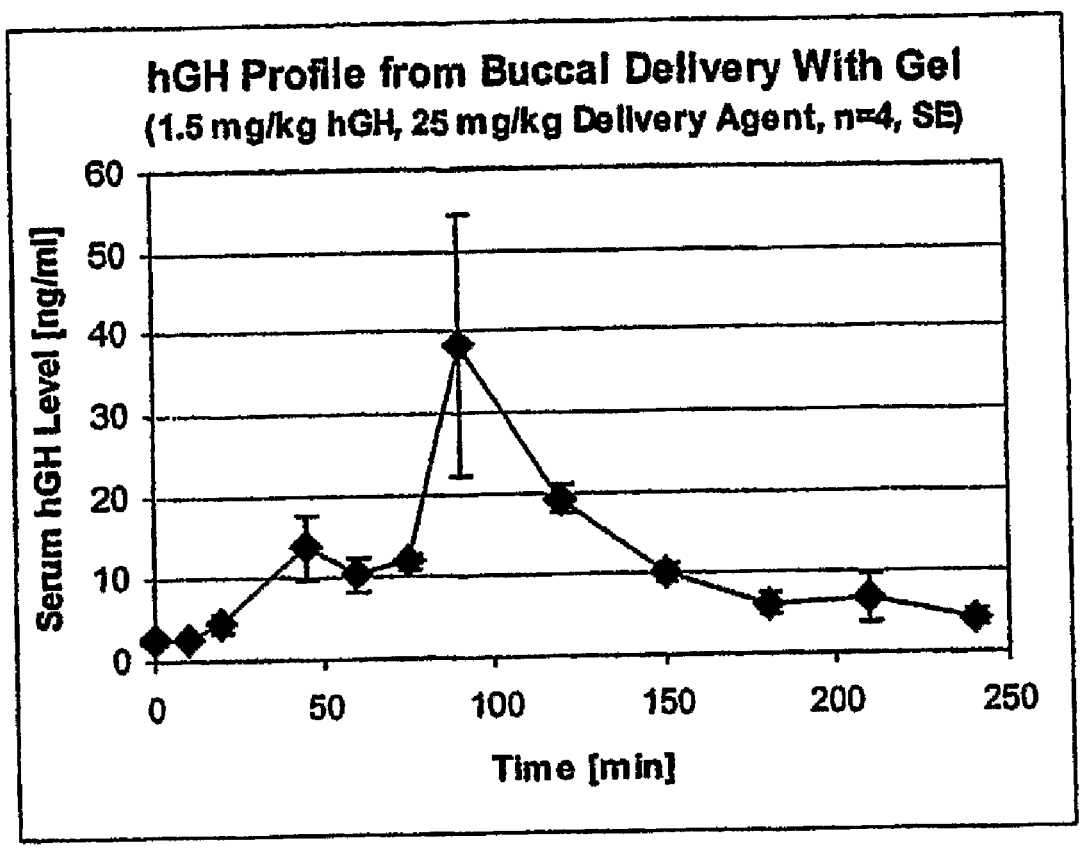
FIG. 4 is a graph of mean human growth hormone (hGH) concentrations over time after buccal administration of a gel dosage form containing 1.5 mg/kg hGH with 25 mg/kg monosodium 8-(4-Hydroxyphenoxy)octanoic acid in beagles.

The mean results of buccal administration of the hGH/Delivery Agent Tablet for Trial A according to the present example are also shown in FIG. 1. The mean results for Trial C are shown in FIG. 2, the results for Trial D are shown in FIG. 3, and the results for Trial E are shown in FIG. 4.

The oral administration of hGH and the delivery agent in both liquid and solid dosage forms, i.e. Trials B and F did not result in any detectable amount of hGH in the serum. Surprisingly, however, buccal administration of the tablet and gel forms resulted in hGH serum concentrations between about 10 ng/ml and about 50 ng/ml over a period of about three hours.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A pharmaceutical composition for buccal administration comprising a delivery agent, hGH, and a pharmaceutically acceptable ingredient for facilitating buccal administration, wherein the delivery agent is selected from 8-(4-hydroxyphenoxy)octanoic acid, N-(8-[2-hydroxybenzoyl]-amino)caprylic acid, N-(10-[2-hydroxybenzoyl]-amino)decanoic acid, N-(8-[2-hydroxy-4-methoxybenzoyl]-amino)caprylic acid, N-(8-[2-hydroxy-5-chlorobenzoyl]-amino)caprylic acid, N-(4-[2-hydroxy-4-chlorobenzoyl]-amino)butanoic acid, and pharmaceutically acceptable salts thereof.

2. The composition of claim 1, wherein the delivery agent is 8-(4-hydroxyphenoxy)octanoic acid, or a pharmaceutically acceptable salt thereof.

3. The composition of claim 1, wherein the delivery agent is N-(8-[2-hydroxybenzoyl]-amino) caprylic acid, or a pharmaceutically acceptable salt thereof.

4. The composition of claim 1, wherein the delivery agent is a sodium salt of N-(8-[2-hydroxybenzoyl]-amino) caprylic acid.

5. The composition of claim 1, wherein the delivery agent is N-(10-[2-hydroxybenzoyl]-amino) decanoic acid, or a pharmaceutically acceptable salt thereof.

6. The composition of claim 1, wherein the delivery agent is a sodium salt of N-(10-[2-hydroxybenzoyl]-amino)decanoic acid.

7. The composition of claim 1, wherein the delivery agent is N-(8-[2-hydroxy-4-methoxybenzoyl]-amino) caprylic acid, or a pharmaceutically acceptable salt thereof.

8. The composition of claim 1, wherein the delivery agent is N-(8-[2-hydroxy-5-chlorobenzoyl]-amino) caprylic acid, or a pharmaceutically acceptable salt thereof.

9. The composition of claim 1, wherein the delivery agent is N-(4-[2-hydroxy-4-chlorobenzoyl]-amino) butanoic acid, or a pharmaceutically acceptable salt thereof.

10. The composition of claim 1, wherein the composition is in the form of a gel.

11. A method of administering a hGH component comprising bucally administering an effective amount of the pharmaceutical composition of claim 1.

12. A method for treating growth hormone deficiency in a patient in need thereof comprising bucally administering an effective amount of the pharmaceutical composition of claim 1.

* * * * *